United States Patent

Lang et al.

Patent Number: 5,457,209
Date of Patent: Oct. 10, 1995

[54] 4-[α(CYANOPHENYL)-1-(1,2,3-TRIAZOLYL)METHYL]-BENZONITRILE

[75] Inventors: Marc Lang, Mulhouse, France; Edmond Differding, Louvain-la Neuve, Belgium; Jaroslav Stanek, Arlesheim, Switzerland

[73] Assignee: Ciba-Geigy Corporation, Ardsley, N.Y.

[21] Appl. No.: 306,864

[22] Filed: Sep. 15, 1994

Related U.S. Application Data

[62] Division of Ser. No. 32,070, Mar. 17, 1993, Pat. No. 5,376,669, which is a division of Ser. No. 805,261, Dec. 9, 1991, Pat. No. 5,227,393.

[30] Foreign Application Priority Data

Dec. 12, 1990 [CH] Switzerland ............. 03923/90

[51] Int. Cl.⁶ ............................................. C07D 249/04
[52] U.S. Cl. .......................................................... 548/255
[58] Field of Search ................................................ 548/255

[56] References Cited

U.S. PATENT DOCUMENTS

| | | | |
|---|---|---|---|
| 4,098,894 | 7/1978 | Bushel | 548/255 |
| 4,609,666 | 9/1986 | Hirsch et al. | 548/255 |
| 4,657,921 | 4/1987 | Frick et al. | 514/383 |
| 4,749,713 | 6/1988 | Bowman et al. | 514/341 |
| 4,757,076 | 7/1988 | Hirsch et al. | 514/277 |
| 4,762,836 | 8/1988 | Hirsch | 514/256 |
| 4,764,376 | 8/1988 | Hirsch et al. | 548/255 |
| 4,845,222 | 7/1989 | Morr et al. | 544/347 |
| 4,916,144 | 4/1990 | Strehlke et al. | 514/326 |
| 4,937,250 | 6/1990 | Bowman et al. | 514/341 |
| 4,957,934 | 9/1990 | Boyle | 514/383 |
| 4,978,672 | 12/1990 | Bowman et al. | 514/383 |
| 4,994,478 | 2/1991 | Kishimoto et al. | 514/364 |
| 5,006,543 | 4/1991 | Boyle | 514/383 |
| 5,021,434 | 6/1991 | Strehlke et al. | 514/341 |
| 5,045,558 | 9/1991 | Strehlke et al. | 514/383 |
| 5,071,861 | 12/1991 | Bowman et al. | 514/332 |
| 5,073,574 | 12/1991 | Lang | 514/381 |
| 5,112,845 | 5/1992 | Bowman et al. | 514/399 |
| 5,227,393 | 7/1993 | Lang et al. | 514/381 |
| 5,246,952 | 9/1993 | Lang | 514/365 |
| 5,352,795 | 10/1994 | Bowman et al. | 548/262.2 |

FOREIGN PATENT DOCUMENTS

| | | |
|---|---|---|
| 0118245 | 9/1984 | European Pat. Off. . |
| 0293978 | 12/1988 | European Pat. Off. . |
| 0299683 | 1/1989 | European Pat. Off. . |
| 0337929 | 10/1989 | European Pat. Off. . |
| 1511195 | 5/1978 | United Kingdom . |
| 1555417 | 11/1979 | United Kingdom . |

OTHER PUBLICATIONS

Jones et al "Estrogen Synthetase Inhibitors 2[1] Comparison of the in Vitro Aromatase Inhibitory Activity for a Variety of Nitrogen Heterocycles Substituted with Diarylmethane or Diarylmethanol Groups" J. Med Chem 1990 vol. 33 (416–429).

Taylor et al "Aromatase Inhibition by 5–Substituted Pryimidines and Dihydropyrimidines" J. Med Chem (1987) vol. 30 pp. 1359–1365.

Biagi et al "1,2,3–Triazoles: Structural Changes on two Effective Inhibitors of the Prostaglandin Synthesis in Vitro" Farmaco—Ed. Sc. vol. 43, pp. 597–611 (1988).

Bhatnagar et al "Highly Selective Inhibitor of Estrogen Biosynthesis by CGS 20267, A New Non–Steroidal Aromatase Inhibitor" J. Steroid Biochem Molec. Biol vol. 37 No. 6, pp. 1021–1027 (1990).

*Primary Examiner*—Patricia L. Morris
*Attorney, Agent, or Firm*—Irving M. Fishman; Karen G. Kaiser

[57] ABSTRACT

Compounds of formula I

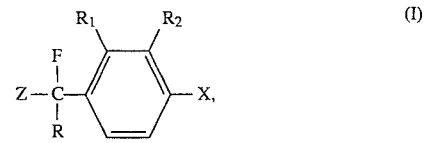

wherein Z, R, $R_1$, $R_2$ and X are as defined in the description, have valuable pharmaceutical properties and are effective especially against tumours. They are prepared in a manner known per se.

1 Claim, No Drawings

4-[α(CYANOPHENYL)-1-(1,2,3-TRIAZOLYL)METHYL]-BENZONITRILE

This is a divisional of Ser. No. 032,070, filed Mar. 17th, 1993, which is a divisional of Ser. No. 805,261, filed Dec. 9th, 1991 now U.S. Pat. No. 5,227,393.

The invention relates to compounds of formula I

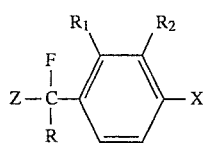

wherein Z is heteroaryl that has one, two, three or four ring nitrogen atoms, each of $R_1$ and $R_2$, independently of the other, is hydrogen or lower alkyl; or $R_1$ and $R_2$ together are $C_3-C_4$alkylene or form a benzo group that is unsubstituted or substituted; R is hydrogen; lower alkyl, aryl or heteroaryl, and X is cyano, carbamoyl, N-mono- or N,N-di-substituted carbamoyl, or hydroxy, lower alkoxy, aryl-lower alkoxy or aryloxy; and wherein X is also halogen when Z is heteroaryl having five ring members; and salts thereof, to a process for the preparation of those compounds, to pharmaceutical compositions that comprise those compounds, to the use of those compounds for the therapeutic treatment of the human or animal body or for the preparation of pharmaceutical compositions.

The compounds of formula I that contain an asymmetric carbon atom may each be in the form of a racemate or in the form of the R- or S-enantiomer. The invention relates to all of these forms and also, for example, to diastereoisomers and mixtures thereof that may occur when two or more centres of asymmetry are present in the molecule, and to geometrical isomers, for example cis- and trans-isomers, when the molecule contains a double bond.

Within the scope of this Application, the general terms used hereinbefore and hereinafter have preferably the following meanings:

The prefix "lower" denotes a radical having up to and including 7, especially up to and including 4, and more especially 1 or 2, carbon atoms.

A heteroaryl radical Z that contains one, two, three or four ring nitrogen atoms is a heterocyclic (azacyclic) radical of aromatic nature and preferably forms a 5- or 6-membered ring, especially a 5-membered ring. It may also, however, be a ring of a different size or may be a 5- or 6-membered ring having one or more fused benzo rings. Heteroaryl Z is bonded either by way of a ring nitrogen atom or by way of a ring carbon atom; 5-membered rings are preferably bonded by way of a ring nitrogen atom, while 6-membered rings are preferably bonded by way of a ring carbon atom.

Heteroaryl Z that has five ring members is preferably imidazolyl, triazolyl or tetrazolyl, but may also be, for example, pyrrolyl, pyrazolyl, indolyl, isoindolyl, benzimidazolyl, benzopyrazolyl or benzotriazolyl, the radicals having a fused benzo ring being bonded by way of their heterocyclic ring.

Heteroaryl Z that has six ring members is preferably pyridyl, pyrimidinyl or pyrazinyl, but may also be, for example, pyridazinyl or triazinyl, quinolinyl or isoquinolinyl, the radicals having a fused benzo ring being bonded by way of their heterocyclic ring.

Heteroaryl Z that has five ring members and that is bonded by way of a ring nitrogen atom is, for example, 1-imidazolyl, 1-(1,2,4-triazolyl), 1-(1,3,4-triazolyl), 1-(1,2,3-triazolyl), 1-tetrazolyl or 2-tetrazolyl, and also, for example, 1-(1,2,5-triazolyl), 1-pyrrolyl, 1-pyrazolyl, 1-indolyl, 1-benzimidazolyl or 1-benzotriazolyl.

Heteroaryl Z that has six ring members and that is bonded by way of a ring carbon atom is, for example, 3-pyridyl, 4-pyridyl, 4-pyrimidinyl, 5-pyrimidinyl or 2-pyrazinyl, and also, for example, 3- or 4-pyridazinyl, 2-pyridyl, 2-pyrimidinyl, 2-(1,3,5-triazinyl), 3-quinolinyl or 4-isoquinolinyl.

Heteroaryl Z that has five ring members and that is bonded by way of a ring carbon atom is, for example, 3-pyrrolyl, 4(5)-imidazolyl, 3-or 4-pyrazolyl, 3-(1,2,4-triazolyl), 4-(1,2,3-triazolyl) or 5-tetrazolyl, and also, for example, 2-pyrrolyl or 3-indolyl.

A heteroaryl radical Z is preferably unsubstituted but may also be substituted, for example, by lower alkyl, hydroxy, lower alkoxy, halogen or trifluoromethyl.

Aryl is, for example, phenyl or naphthyl, such as 1- or 2-naphthyl. The phenyl and naphthyl radicals may be unsubstituted or substituted, especially as indicated below for phenyl. Aryl is preferably phenyl that is unsubstituted or is substituted by one or more, especially from 1 to 4, and more especially one or two, substituents selected from the group consisting of hydrocarbyl, for example lower alkyl, lower alkenyl, lower alkynyl, lower alkylene (attached to two adjacent carbon atoms), cycloalkyl, phenyl-lower alkyl or phenyl; substituted hydrocarbyl, for example lower alkyl substituted, for example, by hydroxy, lower alkoxy, phenyl-lower alkoxy, lower alkanoyloxy, halogen, amino, lower alkylamino, di-lower alkylamino, mercapto, lower alkylthio, lower alkylsulfinyl, lower alkylsulfonyl, carboxy, lower alkoxycarbonyl, carbamoyl, N-lower alkylcarbamoyl, N,N-di-lower alkylcarbamoyl and/or by cyano; hydroxy; etherified hydroxy, for example lower alkoxy, halo-lower alkoxy, phenyl-lower alkoxy, phenyloxy, lower alkenyloxy, halo-lower alkenyloxy, lower alkynyloxy or lower alkylenedioxy (attached to two adjacent carbon atoms); esterified hydroxy, for example lower alkanoyloxy, phenyl-lower alkanoyloxy or phenylcarbonyloxy (≙benzoyloxy); mercapto; etherified mercapto or oxidised etherified mercapto, for example lower alkylthio, phenyl-lower alkylthio, phenylthio, lower alkylsulfinyl [—S(═O)-lower alkyl], phenyl-lower alkylsulfinyl, phenylsulfinyl, lower alkylsulfonyl [—S(O$_2$)-lower alkyl], phenyl-lower alkylsulfonyl or phenylsulfonyl; halogen, nitro, amino; monohydrocarbylamino, for example lower alkylamino, cycloalkylamino, phenyl-lower alkylamino or phenylamino; dihydrocarbylamino, for example di-lower alkylamino, N-lower alkyl-N-phenylamino, N-lower alkyl-N-phenyl-lower alkylamino, lower alkyleneamino or lower alkyleneamino interrupted by—O—,—S— or —NR" (wherein R" is hydrogen, lower alkyl or acyl); acylamino, for example lower alkanoylamino, phenyl-lower alkanoylamino or phenylcarbonylamino (≙ benzoylamino); acyl, for example lower alkanoyl, phenyl-lower alkanoyl or phenylcarbonyl (═benzoyl); carboxy; esterified carboxy, for example lower alkoxycarbonyl; amidareal carboxy, for example carbamoyl, N-lower alkylcarbamoyl, N,N-di-lower alkylcarbamoyl, N,N-lower alkylenecarbamoyl; N,N-lower alkylenecarbamoyl interrupted by —O—,—S— or —NR"—, wherein R" is hydrogen, lower alkyl or lower alkanoyl; N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-hydroxycarbamoyl, N-phenyl-lower alkylcarbamoyl or N-phenylcarbamoyl; cyano, sulfo (SO$_3$H); esterified sulfo, for example lower alkoxysulfonyl; and amidated sulfo, for example sulfamoyl (SO$_2$NH$_2$), N-lower alkylsulfamoyl, N,N-di-lower alkylsulfamoyl or N-phenylsulfamoyl; each phenyl group occurring in the substituents being unsubstituted or substituted by lower alkyl, lower alkoxy, hydroxy, halogen and/or by trifluoromethyl.

An aryl radical R is especially phenyl that is unsubstituted or is monosubstituted, preferably in the 4-position, by cyano, carbamoyl, halogen, lower alkyl, trifluoromethyl, hydroxy, lower alkoxy or by phenyloxy, and is especially 4-cyanophenyl.

Aryl in general is especially phenyl that is unsubstituted or is substituted by lower alkyl, lower alkoxy, hydroxy, halogen and/or by trifluoromethyl, and is most especially unsubstituted phenyl.

Substituted phenyl is preferably mono- or di-substituted and is especially mono-substituted.

A heteroaryl radical R is preferably a 5- or 6-membered heteroaromatic ring to which one or two, especially one, benzo ring(s) is(are) fused and is preferably bonded by way of a ring carbon atom of the benzo ring. It may also, however, be a 5- or 6-membered heteroaromatic aromatic ring without fused benzo rings and may also be bonded by way of a ring carbon or ring nitrogen atom of the heteroaromatic ring. A heteroaryl radical R is unsubstituted or may be substituted - both in the heteroaromatic ring (at ring carbon atoms and/or ring nitrogen atoms therein) and in any benzo ring which may be present - for example by lower alkyl, hydroxy, lower alkoxy, halogen, cyano and/or by trifluoromethyl.

A heteroaryl radical R is especially indolyl, isoindolyl, benzimidazolyl, benzopyrazolyl, benzotriazolyl, benzo[b]furanyl, benzo[b]thienyl, benzoxazolyl or benzothiazolyl, these radicals being unsubstituted or substituted by from 1 to 3 identical or different substituents selected from lower alkyl, hydroxy, lower alkoxy, halogen, cyano and trifluoromethyl. R is especially benzotriazolyl or benzo[b]fumnyl each of which is unsubstituted or is substituted by from 1 to 3 identical or different substituents selected from lower alkyl, halogen and cyano.

Lower alkyl is, for example, n-propyl, isopropyl, n-butyl, isobutyl, sec-butyl, tert-butyl, n-pentyl, neopentyl, n-hexyl or n-heptyl, preferably ethyl and especially methyl.

Lower alkyl substituted by halogen is preferably trifluoromethyl.

Cycloalkyl is preferably $C_3$–$C_8$-and especially $C_3$-or $C_5$–$C_6$-cycloalkyl, which is intended to mean that it contains from 3 to 8, and 3, 5 or 6 ring carbon atoms, respectively.

Halogen is especially chlorine and bromine, but may also be fluorine or iodine.

Carbamoyl is the group—$CONH_2$.

N-mono- or N,N-di-substituted carbamoyl is, for example, N-lower alkylcarbamoyl, N,N-di-lower alkylcarbamoyl, N,N-lower alkylenecarbamoyl; N,N-lower alkylenecarbamoyl interrupted by —O—,—S— or —NR"—, wherein R" is hydrogen, lower alkyl or lower alkanoyl; N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-aryl-lower alkylcarbamoyl, N-arylcarbamoyl or N-hydroxycarbamoyl.

Acyl is preferably lower alkanoyl, for example formyl, acetyl, propionyl, n-butyryl, pivaloyl or valeroyl.

Lower alkylene linked to two adjacent carbon atoms of a benzene ring is preferably $C_3$–$C_4$alkylene, for example 1,3-propylene or 1,4-butylene.

If $R_1$ and $R_2$ together in compounds of formula I are $C_3$–$C_4$alkylene, then these radicals form, together with the benzene ring, an indane- or 1,2,3,4-tetrahydronaphthalene structure. If $R_1$ and $R_2$ together form a benzo group, these radicals form, together with the benzene ring, a naphthalene structure.

Lower alkylenedioxy linked to two adjacent carbon atoms is preferably $C_1$–$C_2$alkylenedioxy, for example methylene- or 1,2-ethylene-dioxy.

Lower alkyleneamino is, for example, $C_4$–$C_7$-and especially $C_4$–$C_5$-alkyleneamino, for example piperidino. Lower alkyleneamino interrupted by —O—,—S— or —NR"— is, for example, $C_4$–$C_7$-and especially $C_4$–$C_5$-alkyleneamino in which a ring carbon atom has been replaced by the corresponding hetero group, and is especially morpholino, thiomorpholino, piperazino or 4-lower alkyl- or 4-lower alkanoyl-piperazino.

N,N-lower alkylenecarbamoyl corresponds to lower alkyleneamino-carbonyl; interrupted N,N-lower alkylenecarbamoyl is defined analogously.

Salts of compounds according to the invention are especially pharmaceutically acceptable non-toxic salts. For example, compounds of formula I having basic groups may form acid addition salts, for example with inorganic acids, such as hydrochloric acid, sulfuric acid or phosphoric acid, or with suitable organic carboxylic or sulfonic acids, for example acetic acid, fumaric acid or methanesulfonic acid, or with amino acids, such as arginine or lysine. Compounds of formula I having an acidic group, for example carboxy, form, for example, metal or ammonium salts, such as alkali metal and alkaline earth metal, for example sodium, potassium, magnesium or calcium, salts, and also ammonium salts with ammonia or suitable organic amines, such as lower alkylamines, for example triethylamine, hydroxy-lower alkylamines, for example 2-hydroxyethylamine, bis(2-hydroxyethyl)amine or tris(2-hydroxyethyl)amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, dibenzylamine or benzyl-β-phenethylamine. Compounds of formula I having an acidic group and a basic group may also be in the form of internal salts, that is to say in zwitterionic form.

For the purpose of isolation or purification it is also possible to use pharmaceutically unsuitable salts, for example picrates or perchlorates. Only the pharmaceutically acceptable non-toxic salts are used therapeutically and these are therefore preferred.

The compounds of formula I according to the invention have valuable, especially pharmacologically useful, properties. In particular, they selectively inhibit the enzyme aromatase in mammals, including humans. As a result, the metabolic conversion of androgens into oestrogens is inhibited. The compounds of formula I are therefore suitable, for example, for the treatment of oestrogen-dependent diseases, including oestrogen-dependent breast cancer, especially in post-menopausal women. They are also useful, for example, in the treatment of gynaecomastia, i.e. breast development in males, since they inhibit the aromatisation of the steroids.

These effects can be demonstrated by in vitro tests or in vivo tests, preferably using mammals, for example guinea pigs, mice, rats, cats, dogs or apes. The dose used is, for example, in a range of approximately from 0.001 to 10 mg/kg, preferably from 0.001 to 1 mg/kg.

The in vitro inhibition of aromatase activity can be demonstrated, for example, by applying the method described in J. Biol. Chem. 249,5364 (1974). It is also possible to obtain $IC_{50}$ values for aromatase inhibition, for example, in vitro from enzyme kinetic studies concerning the inhibition of the conversion of 4–$^{14}$C-androstenedione into 4–$^{14}$C-oestrone in human placental microsomes. The IC$_{50}$ values of the compounds according to the invention are approximately at least 10$^{-9}$ M.

In vivo, aromatase inhibition can be demonstrated, for example, by the suppression of the ovarian oestrogen content of female rats that are injected first with mare's serum gonadotrophin and two days later with human chorionic gonadotrophin, and treated p.o. the following day with a compound of the invention and 1 hour later with androstenedione. A further possible method of determining aromatase inhibition in vivo is as follows: androstenedione (30 mg/kg subcutaneously) is administered on its own or together with a compound of the invention (orally or subcutaneously) for 4 days to sexually immature female rats. After the fourth administration, the rats are sacrificed, and the uteri are isolated and weighed. The aromatase inhibition is determined by the extent to which hypertrophy of the uterus, caused by the administration of androstenedione on its own, is suppressed or reduced by the simultaneous administration of the compound according to the invention. The minimum effective dose of the compounds according to the invention in the in vivo tests is approximately from 0.001 to 1 mg/kg.

The anti-tumour activity, especially in oestrogen-dependent tumours, can be demonstrated in vivo, for example, in DMBA-induced mammary tumours in female Sprague-Dawley rats [cf. Proc. Soc. Exp. Biol. Med. 160,296–301 (1979)]. The use of compounds according to the invention brings about a regression of the tumours and furthermore suppresses the occurrence of new tumours at daily doses of approximately 1 mg/kg and above p.o.

Furthermore, the compounds of formula I do not have an inhibiting effect on cholesterol side-chain cleavage and do not induce adrenal hypertrophy, as is demonstrated by endocrine organ investigations.

Owing to their pharmacological properties as extremely selective inhibitors of the enzyme aromatase, the compounds of formula I are suitable, for example, for the treatment of oestrogen-dependent diseases, such as breast tumours (breast carcinoma), endometriosis, premature labour or endometrial tumours in women, or gynaecomastia in men.

The invention relates preferably to the compounds of formula I wherein Z is imidazolyl, triazolyl, tetrazolyl, pyrrolyl, pyrazolyl, indolyl, isoindolyl, benzimidazolyl, benzopyrazolyl, benzotriazolyl, pyridyl, pyrimidinyl, pyrazinyl, pyridazinyl, triazinyl, quinolinyl or isoquinolinyl, all of these radicals being bonded by way of their heterocyclic ring and all of these radicals being unsubstituted or substituted by lower alkyl, hydroxy, lower alkoxy, halogen or by trifluoromethyl; each of R$_1$ and R$_2$, independently of the other, is hydrogen or lower alkyl; or R$_1$ and R$_2$ together are C$_3$–C$_4$alkylene or form a benzo group that is unsubstituted or is substituted as indicated below for aryl; R is hydrogen, lower alkyl, aryl or heteroaryl, and X is cyano, carbamoyl, N-lower alkylcarbamoyl, N,N-di-lower alkylcarbamoyl, N,N-lower alkylenecarbamoyl; N,N-lower alkylenecarbamoyl interrupted by —O—,—S— or —NR"—, wherein R" is hydrogen, lower alkyl or lower alkanoyl; N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-aryl-lower alkylcarbamoyl, N-arylcarbamoyl, N-hydroxycarbamoyl, hydroxy, lower alkoxy, aryl-lower alkoxy or aryloxy; and wherein X is also halogen when Z is imidazolyl, triazolyl, tetrazolyl, pyrrolyl, pyrazolyl, indolyl, isoindolyl, benzimidazolyl, benzopyrazolyl or benzotriazolyl; wherein aryl is phenyl or naphthyl, these radicals being unsubstituted or substituted by from 1 to 4 substituents selected from the group consisting of lower alkyl, lower alkenyl, lower alkynyl, lower alkylene (attached to two adjacent carbon atoms), C$_3$–C$_8$Cycloalkyl, phenyl-lower alkyl, phenyl; lower alkyl that is in turn substituted by hydroxy, lower alkoxy, phenyl-lower alkoxy, lower alkanoyloxy, halogen, amino, lower alkylamino, di-lower alkylamino, mercapto, lower alkylthio, lower alkylsulfinyl, lower alkylsulfonyl, carboxy, lower alkoxycarbonyl, carbamoyl, N-lower alkylcarbamoyl, N,N-di-lower alkylcarbamoyl and/or by cyano; hydroxy; lower alkoxy, halo-lower alkoxy, phenyl-lower alkoxy, phenyloxy, lower alkenyloxy, halo-lower alkenyloxy, lower alkynyloxy, lower alkylenedioxy (attached to two adjacent carbon atoms), lower alkanoyloxy, phenyl-lower alkanoyloxy, phenylcarbonyloxy, mercapto, lower alkylthio, phenyl-lower alkylthio, phenylthio, lower alkylsulfinyl, phenyl-lower alkylsulfinyl, phenylsulfinyl, lower alkylsulfonyl, phenyl-lower alkylsulfonyl, phenylsulfonyl, halogen, nitro, amino, lower alkylamino, C$_3$–C$_8$cycloalkylamino, phenyl-lower alkylamino, phenylamino, di-lower alkylamino, N-lower alkyl-N-phenylamino, N-lower alkyl-N-phenyl-lower alkylamino; lower alkyleneamino or lower alkyleneamino interrupted by —O—,—S— or —NR" (wherein R" is hydrogen, lower alkyl or lower alkanoyl); lower alkanoylamino, phenyl-lower alkanoylamino, phenylcarbonylamino, lower alkanoyl, phenyl-lower alkanoyl, phenylcarbonyl, carboxy, lower alkoxycarbonyl, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—, wherein R" is hydrogen, lower alkyl or lower alkanoyl; N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-hydroxycarbamoyl, N-phenyl-lower alkylcarbamoyl, N-phenylcarbamoyl, cyano, sulfo, lower alkoxysulfonyl, sulfamoyl, N-lower alkylsulfamoyl, N,N-di-lower alkylsulfamoyl or N-phenylsulfamoyl; each of the phenyl groups occurring in the substituents of phenyl and naphthyl being in its turn unsubstituted or substituted by lower alkyl, lower alkoxy, hydroxy, halogen and/or by trifluoromethyl; wherein heteroaryl is indolyl, isoindolyl, benzimidazolyl, benzopyrazolyl, benzotriazolyl, benzo[b]furanyl, benzo[b]thienyl, benzoxazolyl or benzothiazolyl, these radicals being unsubstituted or substituted by from 1 to 3 identical or different substituents selected from lower alkyl, hydroxy, lower alkoxy, halogen, cyano and trifluoromethyl; and salts thereof.

The invention relates especially preferably to the compounds of formula I wherein Z is imidazolyl, triazolyl, tetrazolyl, pyridyl, pyrimidinyl or pyrazinyl; each of R$_1$ and R$_2$, independently of the other, is hydrogen or lower alkyl; or R$_1$ and R$_2$ together are C$_3$–C$_4$alkylene or form a benzo group; R is hydrogen, lower alkyl, phenyl that is unsubstituted or is substituted by cyano, carbamoyl, halogen, lower alkyl, trifluoromethyl, hydroxy, lower alkoxy, phenyl-lower alkoxy, phenyloxy, lower alkylthio, lower alkylsulfonyl, nitro, di-lower alkylamino, lower alkanoylamino, lower alkanoyl, carboxy, lower alkoxycarbonyl, sulfo, lower alkoxysulfonyl or by sulfamoyl; or is benzotriazolyl or benzo[b]furanyl, the latter two radicals being unsubstituted or substituted by from 1 to 3 identical or different substituents selected from lower alkyl, hydroxy, lower alkoxy, halogen and cyano; and X is cyano, carbamoyl, hydroxy, lower alkoxy, phenyl-lower alkoxy or phenyloxy; and wherein X is also halogen when Z is imidazolyl, triazolyl or tetrazolyl; and salts thereof.

Especially preferred are the compounds of formula I wherein Z is 1-imidazolyl, 1-(1,2,4-triazolyl), 1-(1,3,4-triazolyl), 1-(1,2,3-triazolyl), 1-tetrazolyl, 2-tetrazolyl, 3-pyridyl, 4-pyridyl, 4-pyrimidinyl, 5-pyrimidinyl or 2-pyrazinyl; each of $R_1$ and $R_2$, independently of the other, is hydrogen or lower alkyl; or $R_1$ and $R_2$ together are 1,4-butylene or form a benzo group; R is lower alkyl; phenyl that is unsubstituted or is substituted by cyano, carbamoyl, halogen, lower alkyl, trifluoromethyl, hydroxy, lower alkoxy or by phenyloxy; or is benzotriazolyl or benzo[b]furanyl, the latter two radicals being unsubstituted or substituted by from 1 to 3 identical or different substituents selected from lower alkyl, halogen and cyano; and X is cyano or carbamoyl; and wherein X is also halogen when Z is 1-imidazolyl, 1-(1,2,4-triazolyl), 1-(1,3,4-triazolyl), 1-(1,2,3-triazolyl), 1-tetrazolyl or 2-tetrazolyl; and salts thereof.

Most especially preferred are the compounds of formula I wherein Z is 1-imidazolyl, 1-(1,2,4-triazolyl), 1-(1,2,3-triazolyl), 1-tetrazolyl or 2-tetrazolyl; $R_1$ and $R_2$ are hydrogen; R is phenyl that is unsubstituted or is substituted by cyano or by halogen, or is benzotriazolyl or benzo[b]furanyl, the latter two radicals being unsubstituted or substituted by from 1 to 3 identical or different substituents selected from lower alkyl, halogen and cyano; and X is cyano or halogen; and pharmaceutically acceptable salts thereof.

Prominence is to be given to each of the following as sub-groups of a group of compounds of formula I:

(a) compounds of formula I wherein Z is imidazolyl, triazolyl or tetrazolyl; (b) compounds of formula I wherein Z is 1-imidazolyl, 1-(1,2,4-triazolyl), 1-(1,3,4-triazolyl), 1-(1,2,3triazolyl), 1-tetrazolyl or 2-tetrazolyl; (c) compounds of formula I wherein Z is 1-(1,2,4-triazolyl); (d) compounds of formula I wherein R is 4-cyanophenyl, 4-bromophenyl, 1-methyl-benzotriazol-6-yl, 2,3-dimethyl-7-bromobenzo[b]furan-4-yl or 2,3-dimethyl-7-cyanobenzo[b]furan-4-yl; (e) compounds of formula I wherein R is 4-cyanophenyl or 4-bromophenyl; (f) compounds of formula I wherein $R_1$ and $R_2$ are hydrogen; (g) compounds of formula I wherein X is cyano, bromine or chlorine; and (h) compounds of formula I wherein X is cyano.

The invention relates especially to the specific compounds described in the Examples and to the pharmaceutically acceptable salts thereof.

The compounds of formula I can be prepared in a manner known per se by, for example, (a) reacting a compound of formula II

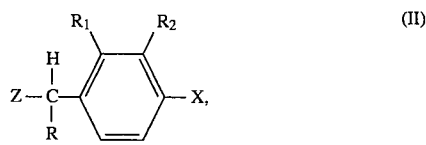

wherein Z, R, $R_1$, $R_2$ and X are as defined under formula I, with a fluorinating agent, or (b) for the preparation of compounds of formula I wherein Z is bonded by way of a ring carbon atom, reacting a compound of formula III

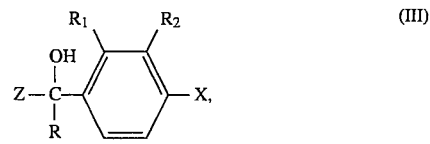

wherein Z, R, $R_1$, $R_2$ and X are as defined under formula I, with a fluorinating agent, or (c) reacting a compound of formula IIIa

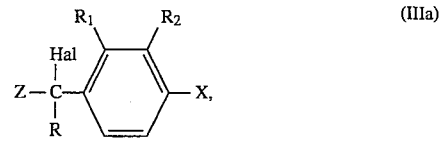

wherein Hal is chlorine, bromine or iodine, and Z, R, $R_1$, $R_2$ and X are as defined under formula I, with a fluorinating agent, or (d) in a compound of formula IV

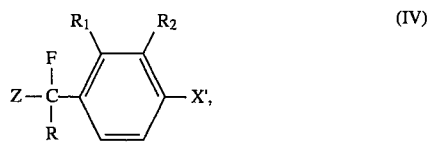

wherein Z, R, $R_1$ and $R_2$ are as defined under formula I and X' is a group that can be converted into a radical X, converting the group X' into the radical X, and/or converting a resulting compound of formula I into a different compound of formula I, and/or converting a resulting salt into the free compound or into a different salt, and/or converting a resulting free compound of formula I into a salt, and/or separating a resulting mixture of isomeric compounds of formula I into the individual isomers.

In the following description of the processes, unless stated otherwise, each of the symbols Z, R, $R_1$, $R_2$ und X is as defined under formula I.

Process (a):

Process (a) is carried out, for example, by convening a compound of formula II by reaction with a strong base, for example an alkali metal diisopropylamide, such as lithium, sodium or potassium diisopropylamide, a hexamethyldisilazane base, such as potassium, sodium or lithium hexamethyldisilazane, or an alkali metal base, such as sec-, tert- or n-butyllithium, into the corresponding carbanion and reacting the latter with an electrophilic fluofinating agent.

There may be mentioned as electrophilic fluorinating agents [see also, for example, L. German and S. Zemskov (ed.), New Fluofinating Agents in Organic Synthesis, Springer, Berlin etc. 1989], for example:

1. Fluorinaring agents with F-halogen bond, for example $F_2$[see, for example, Chem. Rev. 86,997 (1986)]or perchloryl fluoride [$FClO_3$, see, for example, J. Amer. Chem. Soc. 80, 6533 (1958)].

2. Reagents with F-oxygen bond, for example trifluoromethyl hypofluorite [$CF_3OF$, see, for example, Isr. J. Chem. 17,60 (1978)], acetyl hypofluorite [$CH_3COOF$, see, for example, J. Org. Chem. 46,4629 (1981))or trifluoroethyl hypofluorite [$CF_3COOF$, see, for example, J. Org. Chem. 45,4122 (1980)].

3. Reagents with F-nitrogen bond, for example N-F-sulfonamides [see, for example, J. Amer. Chem. Soc. 106,452

(1984) or J. Fluor. Chem. 46,297 (1990)], especially N-fluoro-3,3-dimethyl-2,3-dihydro-1,2-benzothiazole 1,1-dioxide [see, for example, Helv. Chim. Acta 72,1248 (1989)], N-F-sulfonimides [see, for example, J. Amer. Chem. Soc. 109,7194 (1987)], N-F-pyridinium derivatives [see, for example, J. Amer. Chem. Soc. 112,8563 (1990)], especially N-fluoro-2,4,6-trimethylpyridinium trifluoromethylsulfonate, N-F-perfluoropiperidines [see, for example, Chem. and Industry (London) 1964, 1864], N-F-quinuclidinium salts [see, for example, J. Fluor. Chem. 41, 297 (1988) or J. Chem. Soc. Perkin Trans. I 1988,2805], N-F-pyridones [see, for example, J. Fluor. Chem. 26,43 (1984)]or N-F-amides or -lactams [see, for example, J. Org. Chem. 55,3373 (1990)].

4. Reagents with F-noble gas bond, for example xenon difluoride ($XeF_2$) [see, for example, M. Zupan in: S. Patai and Z. Rappoport (ed.), The Chemistry of Functional Groups, Supplement D, Part 2, Wiley, Chichester etc. 1983].

5. Enantioselective fluorinating agents, for example N-fluorosultams derived from camphor [see, for example, Tetrahedron Lett. 29,6087 (1988)], which are suitable especially for the stereoselective fluofination of compounds of formula II in which the central carbon atom is chiral.

The starring compounds of formula II are prepared, for example, as described in EP-A-236 940 or in an analogous manner (see also EP Patent Application No. 90810515.8).

For example, compounds of formula II in which Z is heteroaryl bonded by way of a ring nitrogen atom are prepared by reacting a compound of formula V

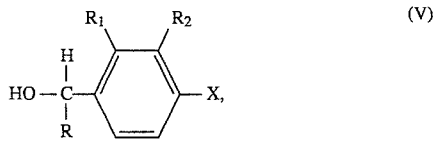

(V)

or especially a reactive esterified derivative thereof, for example a halogen derivative or a lower alkyl- or arylsulfonyloxy derivative, such as methylsulfonyloxy or p-toluenesulfonyloxy, with a compound of formula VI

Z—H (VI), or an N-protected derivative thereof, for example one protected by tri-lower alkylsilyl, lower alkanoyl, N,N-di-lower alkylcarbamoyl or by triphenylmethyl.

The starring compounds of formula V are prepared, for example, by reacting a metallated compound Va

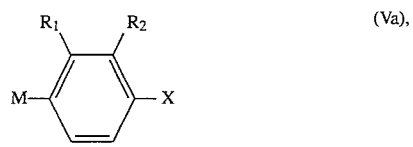

(Va), wherein M is, for example, halomagnesium, copper(I) lithium or, especially, lithium, with an aldehyde R—CHO.

Compounds of formula II can furthermore be prepared, for example, by reacting a compound of formula VII

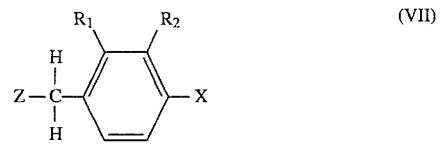

(VII)

under basic conditions with a reactive functional derivative of the radical R, for example a halo-,lower alkyl- or arylsulfonyloxy derivative thereof.

Compounds of formula II wherein Z is heteroaryl bonded by way of a ring carbon atom can furthermore be prepared, for example, by reducing or dehalogenating a compound of formula VIII

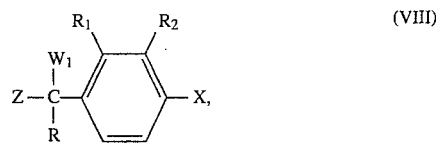

(VIII)

wherein $W_1$ is hydroxy or halogen, respectively. The reduction of $W_1$=OH can be carried out, for example, with tin(II) chloride or glacial acetic acid/aqueous hydriodic acid. The dehalogenation of $W_1$=halogen, for example chlorine, can be effected, for example, with zinc/acetic acid, tributyltin hydride or aluminium amalgam.

The starting compounds of formula VIII wherein $W_1$=OH are prepared, for example, by reaction of an aldehyde or ketone of formula IX

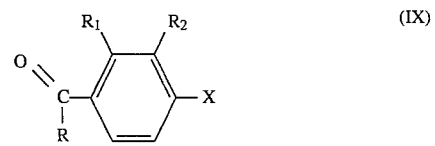

(IX)

with a compound of formula X

Z—$W_2$ (x)

wherein $W_2$ is hydrogen or a protecting group or leaving group, for example tri-lower alkylsilyl or halogen, that is situated at the corresponding ring carbon atom.

The starting compounds of formula VIII wherein $W_1$=halogen are advantageously prepared from the corresponding compounds of formula VIII wherein $W_1$=OH. For that purpose, the latter are reacted with a halogenating agent, for example thionyl chloride.

Compounds of formula II can furthermore be prepared, for example, by reacting a compound of formula XI

(XI)

in a basic medium with a compound of formula XII

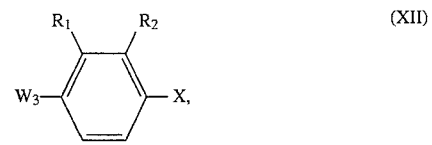

(XII)

wherein $W_3$ is a leaving group, for example halogen, lower alkyl- or aryl-sulfonyloxy and especially fluorine.

A further possible method of preparing compounds of formula II, especially those in which Z is bonded by way of a ring nitrogen atom, comprises converting the radical $W_4$ in a compound of formula XIII

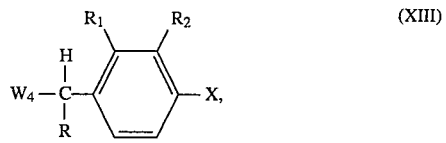

wherein $W_4$ is a radical that can be converted into heteroaryl Z, for example isocyano, amino, azido or hydrazino, into Z by reaction with corresponding ring-forming reagents.

It is also possible, for example, to prepare compounds of formula II from corresponding compounds of formula XIV

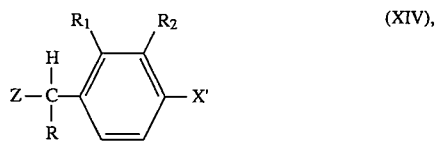

wherein X' is a group that can be converted into a radical X [see under process (d)], by converting the group X' into X.

The starting compounds of formula XIV are prepared, for example, analogously to the processes indicated above for the preparation of compounds of formula II, a radical X' being used in the corresponding reactions instead of the radical X.

The compounds of formula II are valuable intermediates for the preparation of therapeutically valuable fluorine compounds of formula I and, insofar as they are novel, the invention relates to them also. Prominence is to be given here to the following compounds especially:

(a) 4-[α-(4-cyanophenyl)-1-(1,2,3-triazolyl)methyl]-benzonitrile,
(b) 2,3-dimethyl-4-[α-(4-cyanophenyl)-1-(1,2,4-triazolyl)methyl]-7-cyano-benzo[b]furan,
(c) 4-[α-(4-cyanophenyl)-(5-pyrimidinyl)methyl]-benzonitrile,
(d) 4-[α-(4-bromophenyl)-(5-pyrimidinyl)methyl]-benzonitrile,
(e) 2,3-dimethyl-4-[α-(4-cyanophenyl)-(1-imidazolyl)methyl]-7-bromo-benzo[b]furan and
(f) 2,3-dimethyl-4-[α-(4-cyanophenyl)-1-(1,2,4-triazolyl)methyl]-7-bromo-benzo[b]furan, and to salts thereof, more especially to the compound (a) and salts thereof.

The compounds (a), (b), (c), (d), (e) and (f) furthermore have valuable pharmacologically useful properties. They act as aromatase inhibitors in the same manner as the compounds of formula I. Their activity is of the same order of magnitude as that of the compounds of formula I (see above). They too, therefore, are useful, for example, for the treatment of the diseases mentioned above in the case of the compounds of formula I. Like the compounds of formula I, the compounds (a), (b), (c), (d), (e) and (f) can be incorporated in pharmaceutical compositions and used for the treatment of diseases responsive to the inhibition of aromatase and also (for the preparation of pharmaceutical compositions) for the treatment of tumours.

Process (b):

The following fluorinating agents, for example, are suitable for the fluorination of the hydroxy compounds of formula HI: secondary amino-sulfur trifluorides, for example piperidino-sulfur trifluoride or diethylamino-sulfur trifluoride ["DAST", see, for example, J. Org. Chem. 40,574 (1975)]; $SF_4$ (see, for example, Organic Reactions 34, 319, Wiley, New York etc. 1985), for example in the system $SF_4/HF$; fluoroalkylamine reagents of the formula $(R')_2N-CF_2-R$ wherein R' is, for example, ethyl and R is, for example, CHFCl [see, for example, Organic Reactions 21,158, Wiley, New York etc. 1974]; α-fluoro-enamines [see, for example, Tetrahedron Lett. 30,3077 (1989)]; or triethylamine/HF [see, for example, Tetrahedron Lett. 31,6527 (1990)].

The starting compounds of formula III are prepared, for example, by reaction of an aldehyde or ketone of formula IX (see above) with a compound of formula X, $Z-W_2$, wherein $W_2$ is hydrogen or a protecting group or leaving group that is situated at the corresponding ring carbon atom.

Process (c):

Process (c) is concerned, especially, with the replacement of the halogen radicals chlorine, bromine or iodine with a nucleophilic fluorinating agent by nucleophilic substitution. Examples to be mentioned here are potassium fluoride, $KHF_2$ or tetrabutylammonium fluoride [see, for example, J. Org. Chem. 49,3216 (1984)].

The starting compounds of formula IIIa can be prepared, for example, by halogenation of compounds of formula II, for example with an N-halosuccinimide, for example N-bromo- or N-chloro-succinimide, a sulfuryl halide, for example $SO_2Cl_2$, or elemental halogen, for example $Cl_2$ or $Br_2$.

It is also possible, for example, to prepare the starting compounds of formula IIIa by halogenation of compounds of formula III, for example by reaction with a thionyl halide, for example $SOCl_2$ or $SOBr_2$, a phosphorus halide, for example $PBr_3$, $PI_3$ or $PCl_5$, or a hydrohalic acid, for example HBr.

Process (d):

In a compound of formula IV, a group X' that can be convened into the radical X is, for example, halogen, amino, carboxy, lower alkoxycarbonyl, halocarbonyl or an acid anhydride.

X'=halogen, especially bromine, can be converted, for example by reaction with a cyanating agent, for example copper(I) cyanide, into cyano. X'=amino can be converted, for example via diazotisation, for example into halogen, cyano or hydroxy. If X' is carboxy, lower alkoxycarbonyl, halocarbonyl, for example —COCl, or an acid anhydride, then these radicals can be convened by reaction with ammonia or the corresponding primary or secondary amine into carbamoyl or N-mono- or N,N-di-substituted carbamoyl, respectively. The conversion of substituents of aromatic systems in accordance with process (d) is known per se.

In the case where, in a compound of formula IV, the group R contains a substituent that is identical to X', for example when R is—$C_6H_4$—X', the latter can be convened simultaneously upon carrying out process (d).

The starting compounds of formula IV are prepared, for example, analogously to process (a), (b) or (c), using in the corresponding reactions a radical X' instead of the radical X.

Compounds of formula I can be convened into different compounds of formula I.

For example, compounds of formula I wherein X is halogen, especially bromine, can be converted by reaction with hydroxyaryl compounds or corresponding alkali metal salts thereof, for example potassium phenolate, into different compounds of formula I wherein X is aryloxy, advantageously, for example, in the presence of copper.

Furthermore, for example, compounds of formula I wherein X is cyano can be convened by partial hydrolysis, for example with potassium carbonate and aqueous $H_2O_2$ solution, into different compounds of formula I wherein X is carbamoyl.

On the other hand, for example, compounds of formula I wherein X is carbamoyl or N-lower alkylcarbamoyl can be converted, with the removal of water or lower alkanol, respectively, into compounds of formula I wherein X is cyano.

As already explained in process (d), in the reactions described in the three preceding paragraphs, an identical substituent X which may be present in the molecule, for example R=—$C_6H_4$—X, can be converted simultaneously.

Free compounds of formula I having salt-forming properties which are obtainable in accordance with the process can be converted in a manner known per se into their salts, compounds having basic properties being convened, for example, by treatment with acids or suitable derivatives thereof, and compounds having acidic properties being convened, for example, by treatment with bases or suitable derivatives thereof.

Mixtures of isomers obtainable according to the invention can be separated into the individual isomers in a manner known per se, racemates being separated, for example, by forming salts with optically pure salt-forming reagents and separating the mixture of diastereoisomers so obtainable, for example by means of fractional crystallisation.

The reactions mentioned above can be carded out under reaction conditions that are known per se, in the absence or, usually, in the presence of solvents or diluents, preferably those that are inert towards the reagents used and are solvents thereof, in the absence or presence of catalysts, condensing agents or neutralising agents, and, depending on the kind of reaction and/or reactants, at reduced, normal or elevated temperature, for example in a temperature range of from approximately −80° C. to approximately 200° C., preferably from approximately −78° C. to approximately 150° C., more preferably from approximately −20° C. to approximately 150° C., for example at room temperature or the boiling point of the solvent used, under atmospheric pressure or in a closed vessel, where appropriate under pressure, and/or in an inert atmosphere, for example under a nitrogen atmosphere.

In view of the close relationship between the compounds of formula I in free form and in the form of their salts, hereinbefore and hereinafter any reference to the free compounds or their salts should be understood as including also the corresponding salts or free compounds, respectively, where appropriate and expedient.

The compounds, including their salts, may also be obtained in the form of hydrates, or their crystals may, for example, include the solvent used for crystallisation.

The starting materials used in the process of the present invention are preferably those which result in the compounds described at the beginning as being especially valuable.

The invention relates also to those embodiments of the process in which a compound obtainable as an intermediate at any stage of the process is used as starting material and the remaining steps are carried out, or in which a starting material is formed under the reaction conditions or is used in the form of a derivative, for example a salt, thereof.

The present invention relates also to pharmaceutical compositions that comprise one of the pharmacologically active compounds of formula I as active ingredient. Compositions for enteral, especially oral, administration and for parenteral administration are especially preferred. The compositions comprise the active ingredient on its own or, preferably, together with a pharmaceutically acceptable carrier. The dose of the active ingredient depends upon the disease to be treated and upon the species, its age, weight and individual condition, and also upon the mode of administration.

The pharmaceutical compositions comprise from approximately 0.1% to approximately 95% active ingredient, forms of administration that are in single-dose form preferably comprising from approximately 1% to approximately 90% and forms of administration that are not in single-dose form preferably comprising from approximately 0.1% to approximately 20% active ingredient. Unit dose forms, such as dragées, tablets or capsules, comprise from approximately 0.5 mg to approximately 100 mg of active ingredient.

The pharmaceutical compositions of the present invention are prepared in a manner known per se, for example by means of conventional mixing, granulating, confectioning, dissolving or lyophilising processes. For example, pharmaceutical compositions for oral administration can be obtained by combining the active ingredient with one or more solid carriers, if desired granulating a resulting mixture and, if desired, processing the mixture or granules into tablets or dragée cores, where appropriate by adding additional excipients.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starches, for example corn, wheat, flee or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores may be provided with suitable coatings which may be enteric coatings, there being used, inter alia, concentrated sugar solutions which may contain gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Other orally administrable pharmaceutical compositions are dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as corn starch, binders and/or glidants, such as talc or magnesium stearate, and, where appropriate, stabilisers. In soft capsules, the active ingredient is preferably dissolved or suspended in suitable liquid excipients, such as fatty oils, paraffin oil or liquid polyethylene glycols, to which stabilisers may also be added.

Other oral forms of administration are, for example, syrups prepared in customary manner that contain the active ingredient, for example, in suspended form and in a concentration of approximately from 0.01% to 2%, preferably approximately 0.1% or in a similar concentration that provides a suitable single dose when the syrup is administered in quantities of 5 or 10 mi. Also suitable, for example, are powdered or liquid concentrates for the preparation of shakes, for example in milk. Such concentrates may also be packaged in single-dose quantities.

Suitable rectally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols.

For parenteral administration there are suitable, especially, aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, where appropriate, stabilisers. In this case, the active ingredient, if desired together with excipients, may also be in the form of a lyophilisate and be dissolved by the addition of suitable solvents before parenteral administration.

Solutions, such as those used, for example, for parenteral administration, may also be administered in the form of infusion solutions.

The invention relates also to a method for the treatment of the pathological conditions mentioned above, especially oestrogen-dependent pathological conditions, for example for the treatment of a mammal, for example a human, suffering from such a disease and in need of such treatment, for example by the administration to the mammal of an amount of one of the compounds according to the invention that is therapeutically effective against the said diseases. The compounds of the present invention can be administered prophylactically or therapeutically, and are preferably used in the form of pharmaceutical compositions. For a body weight of approximately 70 kg, a daily dose of from approximately 0.5 mg to approximately 100 mg, preferably from approximately 1 mg to approximately 20 mg, of a compound of the present invention will be administered.

The following Examples illustrate the present invention; temperatures are given in degrees Celsius. The following abbreviations are used: ether=diethyl ether; ethyl acetate= acetic acid ethyl ester; THF=tetrahydrofuran; hexane=n-hexane; DMSO=dimethyl sulfoxide; DMF=dimethylformamide; N-fluoro-dimethylsaccharinsultam=N-fluoro-3,3-dimethyl-2,3-dihydro-1,2-benzothiazole 1,1-dioxide; TLC= thin-layer chromatography; MS(FAB)=mass spectrum ("Fast Atom Bombardment").

Example 1

4-[α-(4-cyanophenyl)-α-fluoro-1-(1,2,4-triazolyl)methyl]-benzonitrile

A solution of 0.8 mmol of potassium hexamethyldisilazane in 1.6 ml of toluene is diluted with 5 ml of THF and, after cooling to −78°, a solution of 190 mg of 4-[α-(4-cyanophenyl)-1-(1,2,4-triazolyl)methyl]-benzonitrile (see EP-A-236 940, Ex. 20a) in 3 ml of THF is added thereto. After stirring for 1 hour at the same temperature, there are added dropwise to the dark-red solution 301 mg of N-fluoro-dimethylsaccharinsultam in 3 ml of THF. After a further 1.5 hours at −78°, the reaction mixture is heated to room temperature within 1 hour and poured onto a saturated solution of ammonium chloride in water and then extracted with methylene chloride. Drying over magnesium chloride and concentration of the solvent by evaporation yields the crude product which is purified by means of flash-chromatography (SiO$_2$, hexane/ethyl acetate 9:1, 4:1 to 1:1). TLC (SiO$_2$, CHCl$_3$/methanol 9:1, R$_f$=0.85); IR (KBr): 2220 cm$^{-1}$; $^1$H-NMR (CDCl$_3$):δ(ppm)= 7.46 and 7.76 (8H,m), 8.07 (1H,s), 8.16 (1H,s).

Example 2

4-[α-(4-cyanophenyl)-α-fluoro-(2-tetrazolyl)methyl]-benzonitrile

Analogously to Example 1,4-[α-(4-cyanophenyl)-(2-tetrazolyl)methyl]-benzonitrile (see EP-A-408 509, Ex. 7 and 2) is convened with N-fluoro-dimethylsaccharinsultam into the title compound; m.p. 145°–146°.

Example 3

4-[α-(4,-cyanophenyl)-α-fluoro-(1-tetrazolyl)methyl]-benzonitrile

Analogously to Example 1,4-[α-(4-cyanophenyl)-(1-tetrazolyl)methyl]-benzonitrile (see EP-A-408 509, Ex. 7) is converted with N-fluoro-dimethylsaccharinsultam into the title compound.

Example 4

4-[α-(4-cyanophenyl)-α-fluoro-(1-imidazolyl)methyl]-benzonitrile

Analogously to Example 1,1.075 g of 4-[α-(4-cyanophenyl)-(1-imidazolyl)methyl]-benzonitrile (see EP-A-236 940, Ex. 2a, 3, 4 and 23) are convened with 930 mg of potassium hexamethyldisilazane and 1.7 g of N-fluoro-dimethylsaccharinsultam into the title compound; m.p. 133°, MS(FAB): (M+H)$^+$=303, TLC (methylene chloride/methanol 9:1): R$_f$=0.7.

Example 5

1-methyl-6-[α-(4-chlorophenyl)-α-fluoro- 1-(1,2,4-triazolyl)methyl]-benzotriazole Analogously to Example 1,1-methyl-6-[α-(4-chlorophenyl)- 1-(1,2,4-triazolyl)methyl]benzotriazole (see EP-A-293 978, for example Example 20) is convened with N-fluorodimethylsaccharinsultam into the title compound.

Example 6

4-[α-(4-cyanophenyl)-α-fluoro-1-(1,2,3-triazolyl)methyl]-benzonitrile

Analogously to Example 1,4-[α-(4-cyanophenyl)-1-(1,2, 3-triazolyl)methyl]-benzonitrile is converted with N-fluoro-dimethylsaccharinsultam into the title compound; m.p. 138°–140°.

The starting compound is prepared as follows:

(a) 4-[α-(4-cyanophenyl)-1-(1,2,3-triazolyl)methyl]-benzonitrile

A solution of 640 mg of 4-[1-(1,2,3-triazolyl)methyl]-benzonitrile in 5 ml of DMF is added dropwise over a period of 30 minutes at a constant temperature (25°–26.5°) to a mixture of 1.07 g of potassium tert-butoxide in 5 ml of DMF. After a further 30 minutes at 20°, there is added to the reaction mixture a solution of 525 mg of 4-fluorobenzonitrile in 5 ml of DMF and the reaction mixture is stirred at room temperature for 1.5 hours. It is then cooled to 0°, diluted with CH$_2$Cl$_2$ and neutralised with 6N HCl. The reaction mixture is concentrated and taken up in water/ CH$_2$Cl$_2$, and the aqueous phase is separated. The organic phase is washed with brine, dried over sodium sulfate and concentrated. The crude product is purified by column chromatography (SiO$_2$, toluene to toluene/ethyl acetate 3:1) and crystallised from CH$_2$Cl$_2$/ethanol/hexane to yield the staring compound (a), m.p.>230°; IR (CH$_2$Cl$_2$): 2230, 1605, 1500, 1160 cm$^{-1}$.

The precursor for the preparation of starring compound (a) is prepared as follows:
(1)4-[1-(1,2,3-triazolyl)methyl-benzonitrile 8 g of 1,2,3-triazole, 10.67 g of potassium carbonate and 750 mg of potassium iodide are added in succession to a solution of 15.13 g of 4-bromomethylbenzonitrile in 375 ml of acetone. The reaction mixture is then stirred at 55° for 7.5 hours, and is then cooled and concentrated. The residue is dissolved in $CH_2Cl_2$ and washed in succession with water and brine. After drying over sodium sulfate, the solution is concentrated and the resulting crude product is purified by column chromatography ($SiO_2$, toluene/ethyl acetate 3:19) to yield the precursor (1), IR ($CH_2Cl_2$): 2230, 1615, 1225, 1075 $cm^{-1}$.

Example 7

7-cyano-4-[α-(4-cyanophenyl)-α-fluoro-1-(1,2,4-triazolyl) methyl]-2,3-dimethylbenzo[b] furan Analogously to Example 1,7-cyano-4-[α-(4-cyanophenyl)- 1-(1,2,4-triazolyl)-methyl]- 2,3-dimethylbenzo[b]furan is converted with N-fluoro-dimethylsaccharinsultam into the title compound.

The staring compound is prepared as follows:
(a) 7-cyano-4-[α-(4-cyanophenyl)-1-(1,2,4-triazolyl)methyl]-2,3-dimethylbenzo[b]furan Analogously to Example 6(a), 252 mg of 7-cyano-4-[1-(1,2,4-triazolyl)methyl]-2,3-dimethylbenzo [b]furan (see EP-A-445 073, Ex. 2 and 1 ) are converted with 308 mg of potassium tert-butoxide and 152 mg of 4-fluorobenzonitrile in DMF into the starting compound (a), m.p. (ether/hexane): 200°–202°; IR ($CH_2Cl_2$): 3051, 1613, 1499, 1351, 1104 $cm^{-1}$.

Example 8

4-[α-(4-bromophenyl)-α-fluoro-1-(1,2,4-triazolyl)methyl]-benzonitrile

Analogously to Example 1,4-[α-(4-bromophenyl)- 1-(1, 2,4-triazolyl)methyl]-benzonitrile is converted with N-fluoro-dimethylsaccharinsultam into the title compound.

The starting compound is prepared as follows:
(a) 4-[α-(4-bromophenyl)-1-(1,2,4-triazolyl)methyl]-benzonitrile Analogously to Example 6(a), 190 mg of 1-(4-bromobenzyl)-1,2,4-triazole are convened with 188 mg of potassium tert-butoxide and 106 mg of 4-fluorobenzonitrile into the starting compound (a); $^1$H-NMR ($CDCl_3$): δ=6.73 (1H,s), 7.05 and 7.55 (4H,m), 7.2 and 7.68 (4H,m), 8.02 (1H,s), 8.05 (1H,s).

The precursor for the preparation of starting compound (a) is prepared as follows:
(1 ) 1-(4-bromobenzyl)-1,2,4-triazole A mixture of 1 g of 4-bromobenzyl bromide, 0.41 g of 1,2,4-triazole, 0.55 g of potassium carbonate and 33 mg of potassium iodide in 30 ml of acetone is stirred at 50° for 20 hours. The solid is removed by filtration and the solution is concentrated by evaporation. The resulting crude precursor (1) is purified by column chromatography ($SiO_2$, hexane/ ethyl acetate 1:1) and crystallised from ether; m.p. 77°–79°;$^1$H-NMR ($CDCl_3$):δ=5.3 (2H,s), 7.15 and 7.5 (4H, m), 7.95 (1H,s), 8.08 (1H,m).

Example 9

4-[α-(4-cyanophenyl)-α-fluoro-(5-pyrimidinyl)methyl]-benzonitrile

Analogously to Example 1,4-[α-(4-cyanophenyl)-(5-pyrimidinyl)methyl]-benzonitrile is converted with N-fluoro-dimethylsaccharinsultam into the title compound.

The starting compound is prepared as follows:
(a) 4-[α-(4-cyanophenyl)-(5-pyrimidinyl)methyl]-benzonitrile 1.25 g (5.53 mmol) of tin(II) chloride dihydrate and 3.2 ml of conc. HCl are added to a solution of 863 mg (2.76 mmol) of 4-[α-(4-cyanophenyl)-α-hydroxy-(5-pyrimidinyl) methyl]-benzonitrile [Example 15(b2)]in 10 ml of glacial acetic acid and the reaction mixture is heated under reflux for 2 hours. After cooling, the reaction mixture is poured onto a large quantity of water. The precipitate is filtered off with suction, washed with water, dried and dissolved in 4 ml of THF. 0.23 ml of pyridine is added to this solution which is then stirred at room temperature for 3 hours and filtered, and the filtrate is concentrated by evaporation. The oily residue so obtained is purified by column chromatography (100 g of silica gel, ethyl acetate) and corresponds to the title compound, m.p. 140°–141° (from ether/petroleum ether); $R_f$ value: 0.25 (silica gel/ethyl acetate); IR ($CH_2Cl_2$): 2223 $cm^{-1}$; $^1$H-NMR ($CDCl_3$):δ=5.63 (s,1H); 7.24 (d,4H); 7.68 (d,4H); 8.48 (s,2H); 9.18 (s,1H).

Example 10

4-[α-(4-bromophenyl)-α-fluoro-(5,pyrimidinyl)methyl]-benzonitrile

Analogously to Example 1,4-[α-(4-bromophenyl)-(5-pyrimidinyl)methyl]-benzonitrile is converted with N-fluoro-dimethylsaccharinsultam into the title compound.

The starting compound is prepared as follows:
(a) 4-[α-(4-bromophenyl)-(5-pyrimidinyl)methyl]-benzonitrile Analogously to Example 9a, 4-[α-(4-bromophenyl)-α-hydroxy-(5-pyrimidinyl)methyl]benzonitrile [Example 15(b 1 )]is reduced in glacial acetic acid with tin(II) chloride dihydrate and conc. HCl.

Example 11

4-[α-(4-cyanophenyl)-α-fluoro-(3-pyridyl)methyl]-benzonitrile

Analogously to Example 1,4-[α-(4-cyanophenyl)-(3-pyridyl)methyl]-benzonitrile (see EP-A-236 940, Ex.21 ) is converted with N-fluoro-dimethylsaccharinsultam into the title compound.

Example 12

4-[α(4-cyanophenyl)-α-fluoro-1-(1,2,4-triazolyl)methyl]-benzonitrile 10 ml of THF are cooled to −30°. There are added first 0.17 ml (1.2 mmol) of diisopropylamine and then 0.75 ml (1.2 mmol) of a 1.6M solution of n-butyllithium in hexane and the reaction mixture is cooled to −70°. 285 mg (1 mmol) of 4-[α-(4-cyanophenyl)-1-(1,2,4-triazolyl)methyl]-benzonitrile (see EP-A-236 940, 20a), dissolved in 4 ml of THF, are slowly added dropwise and the reaction mixture is stirred at −70° for 3 hours. 346.8 mg (1.2 mmol) of N-fluoro-2,4,6-trimethylpyridinium trifluoromethylsulfonate are then added, whereupon the previously dark-red-coloured solution slowly decolorises. The reaction mixture is allowed to warm to room temperature, is poured onto a saturated aqueous ammonium chloride solution and extracted with methylene chloride. The organic extracts are dried over magnesium chloride and concentrated by evaporation to yield the crude product which is purified by flash-chromatography ($SiO_2$, hexane/ethyl acetate 9:1, 4:1 to 1:1). TLC ($SiO_2$, $CHCl_3$/methanol 9:1): $R_f$=0.85; IR (KBr): 2220 $cm^{-1}$; $^1$H-NMR ($CDCl_3$): δ=7.46 and 7.76 (8H,m);

8.07 (1H,s), 8.16 (1H,s).

Example 13

7-bromo-4-[α-(4cyanophenyl)-α-fluoro-(1-imidazolyl)methyl]-2,3-dimethylbenzo [b]furan Analogously to Example 1,7-bromo-4-[α-(4-cyanophenyl)-(1-imidazolyl)methyl]-2,3-dimethylbenzo [b]furan is converted with N-fluoro-dimethylsaccharinsultam into the title compound.

The starting compound is prepared as follows:
(a) 7-bromo-4-[α-(4-cyanophenyl)-(1-imidazolyl)methyl]-2,3-dimethylbenzo[b]furan Analogously to Example 6(a), 610 mg of 7-bromo-4-(1-imidazolylmethyl)-2,3-dimethylbenzo[b]furan (see EP-A-445 073, Ex. 3) are converted with 617 mg of potassium tert-butoxide and 303 mg of 4-fluorobenzonitrile in DMF into the starting compound (a) and are crystallised from ether; m.p. 220°–223°; IR ($CH_2Cl_2$): 2231, 1674, 1629, 1490, 1199, 1109 $cm^{-1}$.

Example 14

7-bromo-4-[α(4-cyanophenyl)-α-fluoro-1-(1,2,4-triazolyl)methyl]-2,3-dimethylbenzo [b]furan.

Analogously to Example 1,7-bromo-4-[α-(4-cyanophenyl)- 1-(1,2,4-triazolyl)methyl]-2,3-dimethylbenzo[b]furan is converted with N-fluoro-dimethylsaccharinsultam into the title compound.

The starting compound is prepared as follows:
(a) 7-bromo-4-[α-(4-cyanophenyl)- 1-(1,2,4-triazolyl)methyl]-2,3-dimethylbenzo[b]furan Analogously to Example 6(a), 612 mg of 7-bromo-4-[1-(1,2,4-triazolyl)methyl]-2,3-dimethylbenzo[b]furan (see EP-A-445 073, Ex. 1) are converted with 617 mg of potassium tert-butoxide and 303 mg of 4-fluorobenzonitrile in DMF into the starting compound (a) and crystallised from ether/hexane; m.p. 198°–200°, IR ($CH_2Cl_2$): 2231, 1629, 1498, 1347, 1254, 1200, 1015 $cm^{-1}$.

Example 15

4-[α-(4-cyanophenyl)-α-fluoro-(5-pyrimidinyl)methyl]benzonitrile 0.35 g (2.0 mmol) of piperidino-sulfur trifluoride is added to a solution of 0.62 g (2.0 mmol) of 4-[α-(4-cyanophenyl)-α-hydroxy-(5-pyrimidinyl)methyl]-benzonitrile in 10 ml of 1,2-dichloroethane and the reaction mixture is stirred at 50° for 48 hours. The reaction mixture is washed with water, a saturated sodium hydrogen carbonate solution and again with water, is dried over magnesium sulfate and concentrated by evaporation. The oily residue is purified by column chromatography (100 g of silica gel/ethyl acetate) and corresponds to the title compound, IR ($CH_2Cl_2$): 2220 $cm^{-1}$; $^1$H-NMR ($CDCl_3$): δ=7.20 (d,4H), 7.66 (d,4H), 8.43 (s,2H), 9.15 (s,1H).

The starting compound is prepared as follows:
(a)α,α-bis(4-bromophenyl)-5-pyrimidinemethanol A solution of 20 ml of 1.6N n-butyllithium in hexane is added dropwise within 30 minutes, with stirring and with the exclusion of moisture, to a solution, cooled to −75°, of 5.2 g (33 mmol) of 5-bromopyrimidine and 10.7 g (31.2 mmol) of 4,4'-dibromobenzophenone in 130 ml of THF. The reaction mixture is stirred for a further 0.5 hour at −75° and then for 16 hours at room temperature; then, while cooling with ice, it is hydrolysed by adding 20 ml of water. The organic phase is separated and diluted with ethyl acetate. The solution is washed with 2N HCl and a semi-saturated sodium chloride solution, dried over sodium sulfate, filtered and concentrated by evaporation. The residue is purified by column chromatography (400 g of silica gel, methylene chloride/ethyl acetate 85:15) and recrystallised from ethyl acetate, m.p. 89°–90°, $R_f$ value=0.11 (silica gel, methylene chloride/ethyl acetate 85:15).

(b1)4-[α-(4-bromophenyl)-α-hydroxy-(5-pyrimidinyl)methyl]benzonitrile and
(b2)4-[α-(4-cyanophenyl)-α-hydroxy-(5-pyrimidinyl)methyl]benzonitrile A mixture of 3.7 g (8.8 mmol) of α,α-bis(4-bromophenyl)-5-pyrimidinemethanol and 2.4 g (26.4 mmol) of copper(I) cyanide in 8 ml of DMF is stirred under argon for 4 hours at 160°. The reaction mixture is then cooled to 70°, a solution of 6.4 g (39.6 mmol) of iron(III) chloride in 20 ml of 2N HCl is added dropwise thereto and the resulting mixture is stirred thoroughly at that temperature for 20 minutes. After cooling, extraction is carried out with ethyl acetate. The organic phase is washed with a semi-saturated sodium chloride solution, dried over sodium sulfate and concentrated by evaporation. The residue is purified by column chromatography (200 g of silica gel, hexane/ethyl acetate 1:2) and separated into compounds (b1) and (b2) to yield 4-[α-(4-bromophenyl)-α-hydroxy-(5-pyrimidinyl)methyl]-benzonitrile in the form of a pale-yellow amorphous product, IR ($CH_2Cl_2$): 2190, 3530 $cm^{-1}$, $R_{f\ value}$=0.27 (silica gel, hexane/ethyl acetate 1:2), and 4-[α-(4-cyanophenyl)-α-hydroxy-(5-pyrimidinyl)methyl]-benzonitrile, m.p. 228°–230° (from ethyl acetate), IR (Nujol): 2225, 3150 (broad) $cm^{-1}$, $R_f$ value: 0.14; $^1$H-NMR (DMSO-$d_6$): δ=7.42 (s,1H); 7.55 (d,4H); 7.86 (d, 4H); 8.67 (s,2H); 9.16 (s,1H).

Example 16

4-[α-(4-bromophenyl)α-fluoro-(5-pyrimidinyl)methyl]-benzonitrile

Analogously to Example 15, 4-[α-(4-bromophenyl)-α-hydroxy-(5-pyrimidinyl)methyl]benzonitrile [Example 15(b1)]is reacted in 1,2-dichloroethane with piperidino-sulfur trifluoride.

Example 17

4-[α-(4-cyanophenyl)-α-fluoro-(2-tetrazolyl)methyl]-benzonitrile 399 mg of potassium hexamethyldisilazane are dissolved at −5° in 4 ml of absolute toluene and the solution is diluted with 12 ml of absolute THF. This solution is cooled to −75°, and a solution of 475 mg of 4-[α-(4-cyanophenyl)-(2-tetrazolyl)methyl]-benzonitrile (see EP-A-408 509, Ex. 7 and 2) in 7.5 ml of absolute THF is added dropwise thereto within 10 minutes. The dark-red reaction mixture is stirred for a further hour at the same temperature and then a solution of 0.75 g of N-fluoro-dimethylsaccharinsultam in 7.5 ml of absolute THF is added within 15 minutes, and the reaction mixture is stirred for a further 1.5 hours and then heated to room temperature within 1 hour. The solution is poured onto 50 ml of a saturated, aqueous NaCl solution and extracted with methylene chloride. The organic phase is washed with brine and, after being dried over sodium sulfate, is concentrated. The resulting crude product is stirred three times with ether, purified by column chromatography (silica gel, ethyl acetate/hexane 1:1) and crystallised from hexane; m.p. 145°–146°, MS(FAB): (M+H)$^+$=305, TLC (ethyl acetate/hexane 1:1): $R_f$=0.5.

Example 18

4-[α-(4-cyanophenyl)-α-fluoro-1-(1,2,3-triazolyl)methyl]-benzonitrile

A solution, cooled to −5°, of 798 mg of potassium hexamethyldisilazane in 8 ml of absolute toluene is diluted with 25 ml of absolute THF and cooled to −75°, and a solution of 950 mg of 4-[α-(4-cyanophenyl)-1-(1,2,3-triazolyl)methyl]-benzonitrile (Ex.6a) in 15 ml of absolute THF and 1 ml of absolute DMF is added thereto within 15 minutes. After stirring for 1 hour at −75°, a solution of 1.5 g of N-fluoro-dimethylsaccharinsultam in 15 ml of THF is added. After stirring for a further 1.5 hours, the cooling bath is removed, whereupon the reaction mixture warms to room temperature within 1 hour. The reaction mixture is poured onto 100 ml of a saturated, aqueous ammonium chloride solution and is extracted with methylene chloride. The organic phase is washed with brine, dried over sodium sulfate and concentrated. The resulting crude product is stirred twice with ether and purified by column chromatography (silica gel, ethyl acetate/hexane 1:1 ); m.p. 138°–140°, MS(FAB): (M+H)$^+$=304, TLC (ethyl acetate/hexane 1:1): R$_f$=0.41.

Example 19

10 000 tablets, each containing 5 mg of active ingredient, for example one of the compounds prepared in Examples 1 to 18, are prepared:

| Composition: | |
|---|---|
| active ingredient | 50.00g |
| lactose | 2535.00g |
| corn starch | 125.00g |
| polyethylene glycol 6000 | 150.00g |
| magnesium stearate | 40.00g |
| purified water | quantum satis |

Procedure:

All of the pulverulent constituents are sieved through a sieve of mesh size 0.6 mm. Then, the active ingredient, the lactose, the magnesium stearate and half of the starch are mixed in a suitable mixer. The other half of the starch is suspended in 65 ml of water and the resulting suspension is added to a boiling solution of the polyethylene glycol in 260 ml of water. The resulting paste is added to the powder mixture and the resulting mixture is granulated, if necessary with the addition of more water. The granules are dried overnight at 35°, forced through a sieve of 1.2 mm mesh size and compressed to form tablets having a breaking notch.

Example 20

1000 capsules, each containing 10 mg of active ingredient, for example one of the compounds prepared in Examples 1 to 18, are prepared:

| Composition: | |
|---|---|
| active ingredient | 10.00g |
| lactose | 207.00g |
| modified starch | 80.00g |
| magnesium stearate | 3.00g |

Procedure:

All of the pulverulent constituents are sieved through a sieve of 0.6 mm mesh size. The active ingredient is then mixed, in a suitable mixer, first with the magnesium stearate and then with the lactose and the starch until a homogeneous mixture is obtained. Hard gelatin capsules No. 2 are each filled with 300 mg of the resulting mixture using a capsule-filling machine.

What is claimed is

1. 4[a-(cyanophenyl)-1-(1,2,3,-triazolyl)methyl]-benzonitrile or a salt thereof.

* * * * *

UNITED STATES PATENT AND TRADEMARK OFFICE
CERTIFICATE OF CORRECTION

PATENT NO. : 5,457,209
DATED : OCTOBER 10TH, 1995
INVENTOR(S) : LANG ET AL

It is certified that error appears in the above-indentified patent and that said Letters Patent is hereby corrected as shown below:

In claim 1, column 22, line 33 delete "4[a-(cyanophenyl)-1-(1,2,3,-triazolyl)" and insert —4[$\alpha$-(cyanophenyl)-1-(1,2,3-triazolyl)— in lieu thereof.

Signed and Sealed this

Twentieth Day of February, 1996

BRUCE LEHMAN

Attest:

Attesting Officer

Commissioner of Patents and Trademarks